United States Patent
Chen et al.

(10) Patent No.: US 9,518,301 B2
(45) Date of Patent: Dec. 13, 2016

(54) APTAMER FOR DETECTION OF ALPHA-METHYLACYL-COA RACEMASE AND DIAGNOSTIC KIT THEREOF

(71) Applicant: NATIONAL TAIWAN UNIVERSITY, Taipei (TW)

(72) Inventors: Lin-Chi Chen, Taipei (TW); Deng-Kai Yang, Taipei (TW); Chun-Hua Hsu, Taipei (TW); Ming-Ying Lee, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 14/742,681

(22) Filed: Jun. 17, 2015

(65) Prior Publication Data

US 2016/0177397 A1    Jun. 23, 2016

(30) Foreign Application Priority Data

Dec. 18, 2014  (TW) .............................. 103144281 A

(51) Int. Cl.
| | | |
|---|---|---|
| *C12N 9/16* | (2006.01) | |
| *C12Q 1/68* | (2006.01) | |
| *C12N 15/115* | (2010.01) | |

(52) U.S. Cl.
CPC ........... *C12Q 1/6886* (2013.01); *C12N 15/115* (2013.01); *C12N 2310/16* (2013.01)

(58) Field of Classification Search
None
See application file for complete search history.

(56) References Cited

PUBLICATIONS

Yang et al, Selection of Aptamers for Fluorescent Detection of Alpha-Methylacyl-CoA Racemase by Single-bead SELEX, published online Jun. 19, 2014, Biosensors and Bioelectronics, 62: 106-11262: 106-112 and Supplementary Materials, pp. 1-6.*

Ferdinandusse S, Denis S, IJlst L, Dacremont G, Waterham HR, Wanders RJ. Subcellular localization and physiological role of alpha-methylacyl-CoA racemase. J Lipid Res. Nov. 2000;41(11):1890-6.

Jiang Z, Woda BA, Rock KL, Xu Y, Savas L, Khan A, et al. P504S: a new molecular marker for the detection of prostate carcinoma. Am J Surg Pathol. Nov. 2001;25(11):1397-404.

Xu J, Stolk JA, Zhang X, Silva SJ, Houghton RL, Matsumura M, et al. Identification of differentially expressed genes in human prostate cancer using subtraction and microarray. Cancer Res. Mar. 15, 2000;60(6):1677-82.

Zhou M, Chinnaiyan AM, Kleer CG, Lucas PC, Rubin MA. Alpha-Methylacyl-CoA racemase: a novel tumor marker overexpressed in several human cancers and their precursor lesions. Am J Surg Pathol. Jul. 2002;26(7):926-31.

Rogers CG, Yan G, Zha S, Gonzalgo ML, Isaacs WB, Luo J, et al. Prostate cancer detection on urinalysis for alpha methylacyl coenzyme a racemase protein. J Urol. Oct. 2004;172(4 Pt 1):1501-3.

Zielie PJ, Mobley JA, Ebb RG, Jiang Z, Blute RD, Ho SM. A novel diagnostic test for prostate cancer emerges from the determination of alpha-methylacyl-coenzyme a racemase in prostatic secretions. J Urol. Sep. 2004;172(3):1130-3.

Sreekumar A, Laxman B, Rhodes DR, Bhagavathula S, Harwood J, Giacherio D, et al. Humoral immune response to alpha-methylacyl-CoA racemase and prostate cancer. J Natl Cancer Inst. Jun. 2, 2004;96(11):834-43.

Ellington AD, Szostak JW. In vitro selection of RNA molecules that bind specific ligands. Nature. Aug. 30, 1990;346 (6287):818-22.

Tuerk C, Gold L. Systematic evolution of ligands by exponential enrichment: RNA ligands to bacteriophage T4 DNA polymerase. Science. Aug. 3, 1990;249(4968):505-10.

Nimjee SM1, Rusconi CP, Sullenger BA. Aptamers: an emerging class of therapeutics. Annu Rev Med. 2005;56:555-83.

Prior C1, Guillen-Grima F, Robles JE, Rosell D, Fernandez-Montero JM, Agirre X, et al. Use of a combination of biomarkers in serum and urine to improve detection of prostate cancer. World J Urol. Dec. 2010;28(6):681-6.

* cited by examiner

*Primary Examiner* — Kate Poliakova-Georgantas
(74) *Attorney, Agent, or Firm* — Hannah M. Tien

(57) ABSTRACT

The present invention provides an alpha-methylacyl-CoA racemase binding aptamers. The present invention further provides a kit for detecting alpha-methylacyl-CoA racemase or cancer in a sample, which comprises the above-mentioned alpha-methylacyl-CoA racemase binding aptamers.

3 Claims, 16 Drawing Sheets
(1 of 16 Drawing Sheet(s) Filed in Color)

FIGURES

SEQUENCE LISTING

```
<160> NUMBER OF SEQ ID NOS: 9

<210> SEQ ID NO 1
<211> LENGTH: 20
<212> TYPE: PRT
<213> ORGANISM: Artificial Sequence
<220> FEATURE:
<223> OTHER INFORMATION: 6xhis tag

<400> SEQUENCE: 1

Met Gly Ser Ser His His His His His His Ser Ser Gly Leu Val Pro
1               5                   10                  15

Arg Gly Ser His
            20

<210> SEQ ID NO 2
<211> LENGTH: 60
<212> TYPE: DNA
<213> ORGANISM: Artificial Sequence
<220> FEATURE:
<223> OTHER INFORMATION: Artificial single-stranded DNA library
<220> FEATURE:
<221> NAME/KEY: misc_feature
<222> LOCATION: (16)..(45)
<223> OTHER INFORMATION: n is a, c, g, or t

<400> SEQUENCE: 2
ccctacggcg ctaacnnnnn nnnnnnnnnn nnnnnnnnnn nnnnngccac cgtgctacaa      60

<210> SEQ ID NO 3
<211> LENGTH: 15
<212> TYPE: DNA
<213> ORGANISM: Artificial Sequence
<220> FEATURE:
<223> OTHER INFORMATION: Forward primer

<400> SEQUENCE: 3
ccctacggcg ctaac                                                      15

<210> SEQ ID NO 4
<211> LENGTH: 15
<212> TYPE: DNA
<213> ORGANISM: Artificial Sequence
<220> FEATURE:
<223> OTHER INFORMATION: Reversed primer

<400> SEQUENCE: 4
ttgtagcacg gtggc                                                      15

<210> SEQ ID NO 5
<211> LENGTH: 60
<212> TYPE: DNA
<213> ORGANISM: Artificial Sequence
<220> FEATURE:
<223> OTHER INFORMATION: Aptamer AMC51
```

```
<400> SEQUENCE: 5
ccctacggcg ctaacccatg ctacgaattc gttgttaaac aataggccac cgtgctacaa    60

<210> SEQ ID NO 6
<211> LENGTH: 60
<212> TYPE: DNA
<213> ORGANISM: Artificial Sequence
<220> FEATURE:
<223> OTHER INFORMATION: Aptamer AMC55

<400> SEQUENCE: 6
ccctacggcg ctaaccagta tgttccggat tggagagctc ctgttgccac cgtgctacaa    60

<210> SEQ ID NO 7
<211> LENGTH: 60
<212> TYPE: DNA
<213> ORGANISM: Artificial Sequence
<220> FEATURE:
<223> OTHER INFORMATION: Aptamer AMC56

<400> SEQUENCE: 7
ccctacggcg ctaacccagc tactctagaa cccattatat tttgggccac cgtgctacaa    60

<210> SEQ ID NO 8
<211> LENGTH: 60
<212> TYPE: DNA
<213> ORGANISM: Artificial Sequence
<220> FEATURE:
<223> OTHER INFORMATION: Aptamer AMC68

<400> SEQUENCE: 8
ccctacggcg ctaaccatga cgaattgtgt atatatcaat actcggccac cgtgctacaa    60

<210> SEQ ID NO 9
<211> LENGTH: 60
<212> TYPE: DNA
<213> ORGANISM: Artificial Sequence
<220> FEATURE:
<223> OTHER INFORMATION: Aptamer AMC69

<400> SEQUENCE: 9
ccctacggcg ctaacactac tcttccggat gaagctctta tgttggccac cgtgctacaa    60
```

APTAMER FOR DETECTION OF ALPHA-METHYLACYL-COA RACEMASE AND DIAGNOSTIC KIT THEREOF

CROSS-REFERENCES TO RELATED APPLICATIONS

The present application claims priority to Taiwan Patent Application No. 103144281 filed on Dec. 18, 2014, incorporated herein by reference in its entirely. The sequence listing text file, file name 2386-NTU-US_ST25 created Jun. 16, 2015, file size 2151 bytes, is incorporated herein by reference in its entirely.

FIELD OF THE INVENTION

The present invention relates to an artificial aptamer. Particularly, the invention relates to an aptamer for detecting alpha-methylacyl-CoA racemase. The present invention also relates to a diagnostic kit for detecting alpha-methylacyl-CoA racemase or cancer in a sample.

BACKGROUND OF THE INVENTION

Alpha-methylacyl CoA racemase (AMACR also known as P504S) is a metabolic enzyme that plays an important role in chiral conversion catalysis in the mitochondrial β-oxidation pathway for fatty acid catabolism and converts several (2R)-methyl-branched-chain fatty acyl-CoAs to their (S)-stereoisomers (J Lipid Res. 2000 November; 41 (11); 1890-6). AMACR has been proven to be highly expressed in prostate cancer cells and has become a novel protein biomarker for prostate cancer diagnosis (Am J Surg Pathol. 2001 November; 25 (11); 1397-404 and Cancer Res. 2000 Mar. 15; 60 (6): 1677-82). In addition, over production of AMACR would be linked to breast, colorectal, renal and other cancers in addition to prostate cancer (Am J Surg Pathol. 2002 July; 26 (7): 926-31). All of these evidences suggest that AMACR is a potent cancer biomarker and can play a synergistic role for early diagnosis of the prostate cancer. Although AMACR is a mitochondrial enzyme, there are some studies showing the possibilities of carrying out non-invasive AMACR assays directly from urine (J Urol. 2004 October; 172(4 Pt 1): 1501-3), prostate secretion (J Urol. 2004 September; 172(3) 1130-3), and blood (J Natl Cancer Inst. 2004 Jun. 2; 96 (11): 834-43) samples of the prostate cancer patients. Thus, the R&Ds of assays and sensors for detecting AMACR proteins in cancer cells or body fluids have attracted broad attention. The AMACR assay or sensor studies reported so far all relied on the use of anti-AMACR IgG antibodies as recognition elements, which are costly and have a limited shelf-life for biosensor development and production.

Aptamers are single-stranded oligonucleotides that can bind to a wide range of targets, from amino acids, drugs, proteins or even whole cells, with high affinity and specificity. In 1990, they are first selected by an in vitro selection process call SELEX (systematic evolution of ligands by exponential enrichment) (Nature. 1990 Aug. 30; 346(6287): 818-22 and Science. 1990 Aug. 3; 249(4968):505-10). The process involves repeated rounds of purification from a combinatorial library of nucleic acid. Nowadays, aptamers are promising candidates for antibodies because they have several advantages that offer the possibility to overcome the limitation of antibodies, such as their rapid and easier synthesis, the capability of chemical modification, and the non-immunogenic characterization (Annu Rev Med. 2005; 56:555-83). This is an important property for application of aptamers in clinics. Although SELEX is a common practice for in vitro selection of DNA aptamers, that could still be a daunting task when the target protein is AMACR, which is a precious and costly protein. Therefore, an ordinary SELEX protocol that might consume several milligrams of protein to accomplish all SELEX rounds is not considered viable here. As illustrated in FIG. 1A, to select AMACR recognition DNA aptamers, the glass micro beads with a size of 500 μm are chosen so that the single-bead manipulation can be simply carried out by tweezers without the sophisticated instrumentation. Silane chemistry is adopted for modifying the glass bead surface with epoxide functionality for covalent immobilization of AMACR. The SELEX protocol developed in this work is rapid and consumes tiny amount of costly AMACR for accomplishing the aptamer selection rounds.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SUMMARY OF THE INVENTION

Figure 1A:
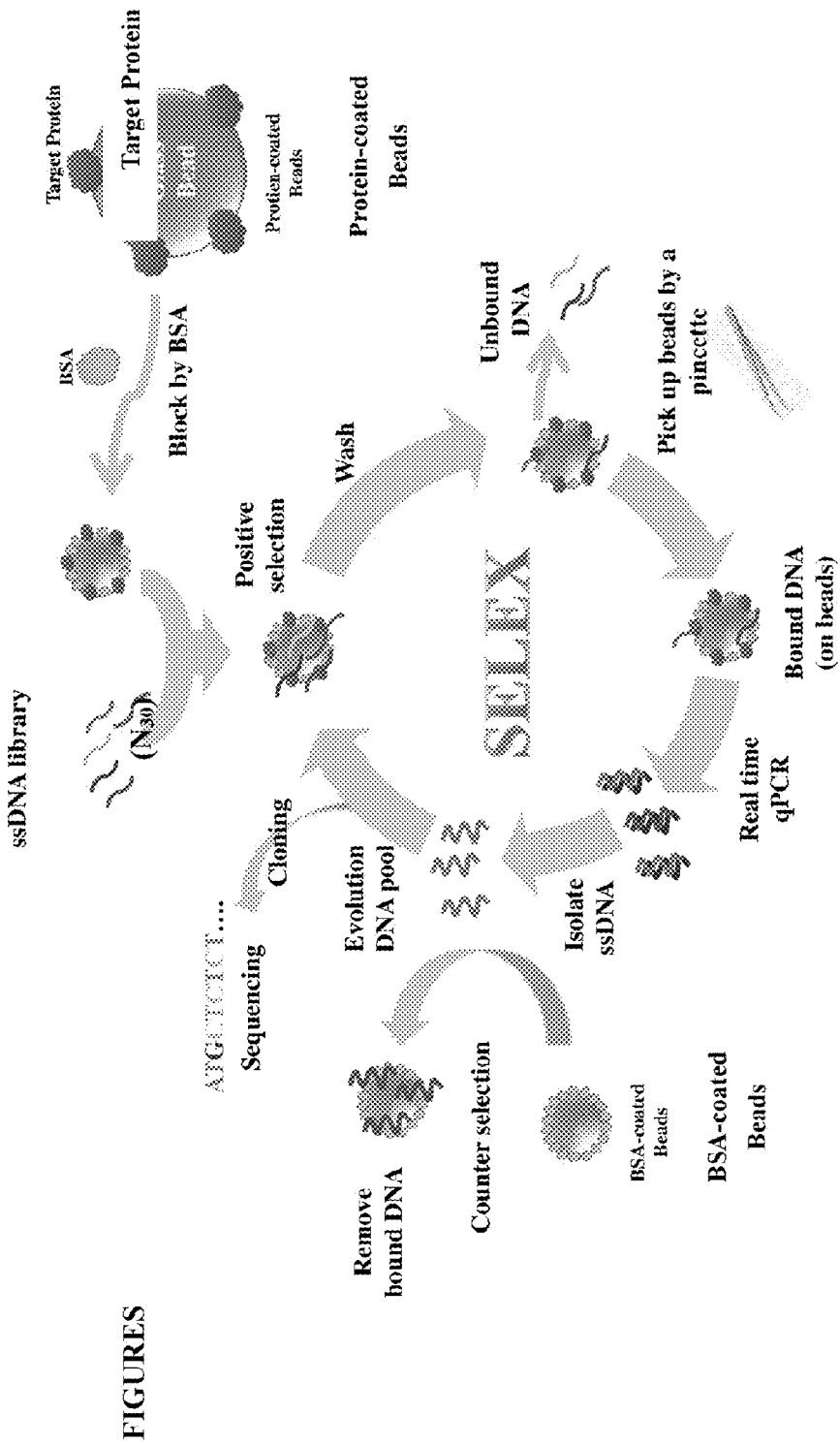
FIG. 1A shows a schematic illustration of the single-bead SELEX protocol of the present invention for generation of AMACR binding aptamers.

The present invention relates to an alpha-methylacyl-CoA racemase binding aptamer consisting of the nucleotide sequences group of SEQ ID NO: 5, SEQ ID NO: 6, SEQ ID NO: 7, SEQ ID NO: 8, and SEQ ID NO: 9. The present invention also relates to a kind of diagnostic kit for detecting alpha-methylacyl-CoA racemase or cancer in a sample, which comprises the above-mentioned alpha-methylacyl-CoA racemase binding aptamer.

DETAILED DESCRIPTION OF THE INVENTION

The present invention provides an AMACR binding aptamer.

In a specific embodiment, the present invention provides the AMACR binding aptamer screened by using single-bead SELEX. The AMACR binding aptamer is selected from SEQ ID NO: 5, SEQ ID NO: 6, SEQ ID NO: 7, SEQ ID NO: 8, or SEQ ID NO: 9. The aptamers are highly specific to AMACR.

In a specific embodiment, the present invention provides the AMACR binding aptamer with a GC content greater than 50%.

In a specific embodiment, the present invention provides the AMACR binding aptamer with delta Gibbs free energy (A G) between −4.3 kcal/mol and −8.9 kcal/mol indicating that these aptamer structures are stable secondary structure.

In another specific embodiment of the present invention, AMC55 is least able to form a stable B-form or stem-loop binding motif when compared to the other two. In addition, AMC51 has more obvious (more stable) B-form character-istics than AMC56 in a comparison of SEQ ID NO: 5 (AMC51), SEQ ID NO: 6 (AMC55), and SEQ ID NO: 7 (AMC56).

In a specific embodiment, the present invention provides the AMACR binding aptamer having a dissociation constant in a range from about 25±13 nM to 280±314 nM for a binding event between the alpha-methylacyl-CoA racemase and the aptamer.

In a preferred embodiment, the present invention provides apparent dissociation constants (KD) for the binding events between AMACR and AMC 51, AMC55, and AMC56 estimated to be 49±26 nM, 139±157 nM, and 65±31 nM, respectively. The aptamers of the present invention have a high affinity with AMACR, and the trend is positively correlated with the stability of the secondary structure.

In a specific embodiment, the AMACR binding aptamers of the invention do not bind to non-target proteins, such as bovine serum albumin (BSA), human serum albumin (HSA), total protein in fetal bovine serum (FBS), and other recombinant E. coli proteins like hemagglutinin 1 (H1), hemagglutinin 5 (H5). The aptamers of the invention are highly specific to AMACR.

The present invention further provides a kit for detecting alpha-methylacyl-CoA racemase or cancer in a sample, which comprises the above-mentioned alpha-methylacyl-CoA racemase binding aptamer, wherein the aptamer selected from SEQ ID NO: 5, SEQ ID NO: 6, SEQ ID NO: 7, SEQ ID NO: 8, or SEQ ID NO: 9.

As used herein, the term "cancer" is a class of diseases which occurs because cells become immortalized; AMACR is highly expressed in the cells. In a specific embodiment it refers to therioma, including, but not limited to, colorectal cancer or prostate cancer.

The kit in a specific embodiment of the present invention, the detecting of alpha-methylacyl-CoA racemase is in the limitation from 0.22 nM to 0.88 nM or from 9.75 ng/mL to 39 ng/mL.

The kit in a preferred embodiment of the present invention, the limit of detection (LOD) of the ELAA detection is determined to be as low as 0.44 nM or 19.5 ng/mL.

The kit in a specific embodiment of the present invention, the aptamers are responsive to the cellular lysate (total protein) of a common prostate cancer cell line 22Rv1 that overexpresses AMACR. The kit meets the requirement of AMACR detection for the application in prostate cancer diagnosis.

The kit in another specific embodiment of the present invention, the aptamers are responsive to the cellular lysate (total protein) of a common prostate cancer cell line (LNCaP and PC3) that overexpresses AMACR. The kit meets the requirement of AMACR detection for the application in prostate cancer diagnosis. Moreover, the kit can successfully identify the expression amounts of AMACR among different prostate cancer cell lines.

In a preferred embodiment of the present invention, the aptamers can identify the expression amounts of AMACR among different prostate cancer cell lines, and have a potential to replace the role of AMACR antibody for use in prostate cancer diagnostics.

In a specific embodiment, the AMACR binding aptamers of the present invention are labeled with a label compound. The label compound is selected from the group consisting of a radioisotope (e.g., $^{125}$I, $^{131}$I, $^{35}$S, $^{3}$H, or $^{32}$P), an enzyme (e.g., alkaline phosphatase, horseradish peroxidase, luciferase, or β-galactosidase), a fluorescent tag (e.g., fluorescein, rhodamine, phycoerythrin, GFP, or BFP), a chemiluminescent tag (e.g., Qdot™, Provided by Quantum Dot Corporation, Palo Alto, Calif.), and a magnetic substance.

As used herein, the term "a" or "an" are employed to describe elements and components of the invention. This is done merely for convenience and to give a general sense of the invention. This description should be read to include one or at least one and the singular also includes the plural unless it is obvious that it is meant otherwise.

As used herein, the term "or" are employed to describe "and/or".

As used herein, the term "sample" is selected from the group consisting of a tissue sample, a fecal sample, a urine samples, a cell homogenate, a blood sample, one or more biological fluids, or any combinations thereof.

The terms used in the description herein will have their ordinary and common meaning as understood by those skilled in the art, unless specifically defined otherwise.

EXAMPLES

The examples below are non-limiting and are merely representative of various aspects and features of the present invention.

Example 1

Materials and Methods

Reagents

Bovine serum albumin (BSA), acid-washed glass bead, (3glycidyloxypropyl) trimethoxy-silane (GLYMO), RIPA buffer, and 3,3',5,5'-tetramethylbenzidine (TMB) were all purchased from Sigma-Aldrich (St. Louis, Mo.). Commercial AMACR protein human recombinant was purchased from ProSpec-Tany TechnoGene (Rehovot, Israel), and homemade recombinant AMACR protein was also prepared for comparison. AMACR antibody (2A10F3, mouse monoclonal) and HRP-conjugated goat anti-mouse IgG polyclonal antibody were purchased from GeneTex (Hsinchu, Taiwan). All the other reagents were of analytical grade. $E.\ coli$ Top10F' (Invitrogen) was used for vector construction and DNA manipulation, $E.\ coli$ expression strain Rosetta (DE3) (Stratagene), vectors pET23a purchased from Novagen were used for protein expression. All other buffers and reagents are of the highest commercial purity.

Preparation of Epoxide-Functionalized Glass Microbeads (EGBs), Homemade Recombinant AMACR Protein, and AMACR Coating In the present embodiment, commercial recombinant AMACR was used for the single-bead SELEX. However, homemade recombinant AMACR protein to perform a series of affinity and specificity assays for the selected aptamers and to see if the aptamers selected against the commercial AMACR would recognize the homemade AMACR as well. The AMACR was expressed from the sequence of isoform CRA_c of AMACR (gb|EAX10818.1|) with a 6xhis tag and other 14 amino acids (MGSSHHHHHHSSGLVPRGSH) (SEQ ID NO: 1) at N-terminal end according to standard recombinant DNA technology using the pET-28 as a vector and $Escherichia\ coli$ as the host cell.

Glass microbeads (500 μm) were cleaned with a piranha solution (1:4 mixture of 30% $H_2O_2$ and concentrated $H_2SO_4$) for 60 min and then rinsed by 95% ethanol and dried at 60° C. in an oven for 1 h. 3-Glycidoxypropyl-trimethoxy silane (GLYMO) was diluted in toluene to yield a concentration of 4% (v/v). The beads were immersed in the GLYMO solution at 30° C. in an oven overnight, then rinsed by 95% ethanol, and dried at 40° C. Fourier transform infrared spectroscopy (FTIR) was used to characterize the functional epoxide group on the bead surface. The FTIR spectra of the modified beads were obtained in the range of wave number from 4000 to 650 $cm^{-1}$ during 256 scans with 4 $cm^{-1}$ resolution with uncoated-glass beads as a blank. The AMACR binding capacity of the EGBs was estimated as follows. First, the EGBs (30 mg=ca. 200 spheres) were coated with an AMACR solution (ca. 1 μg protein dissolved in 30 μL of selection buffer, 50 mM Tris/HCl, 100 mM NaCl, 4 mM KCl, 2.5 mM $MgCl_2$ and 1 mM $CaCl_2$, pH7.4) at 4° C. overnight. After coating, the amount of unbound AMACR in the supernatant was measured by the Bradford assay. Then the amount of AMACR bound on the beads was estimated by subtracting the above value from the initial amount of AMACR loading, and the average AMACR coating amount on each EGB could be estimated as well. Before SELEX, the same condition was used for AMACR coating on to the EGBs, but the AMACR-coated EGBs were blocked with 1% (w/v) BSA in 200 μL of the selection buffer by overnight incubation at 4° C. A similar condition (except for the use of BSA) was adopted to prepare the BSA-coated EGBs for the counter selection and a control experiment in the differential qPCR analysis for the ligand evolution.

Results

Figure 2A:
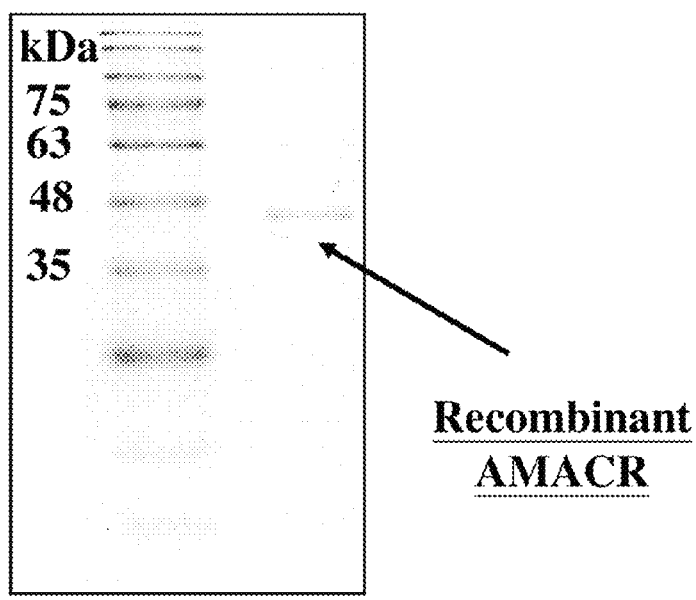
FIG. 2A shows SDS-PAGE (12% gel, Coomassie Blue staining) tests of the homemade recombinant AMACR.
Figure 2B:
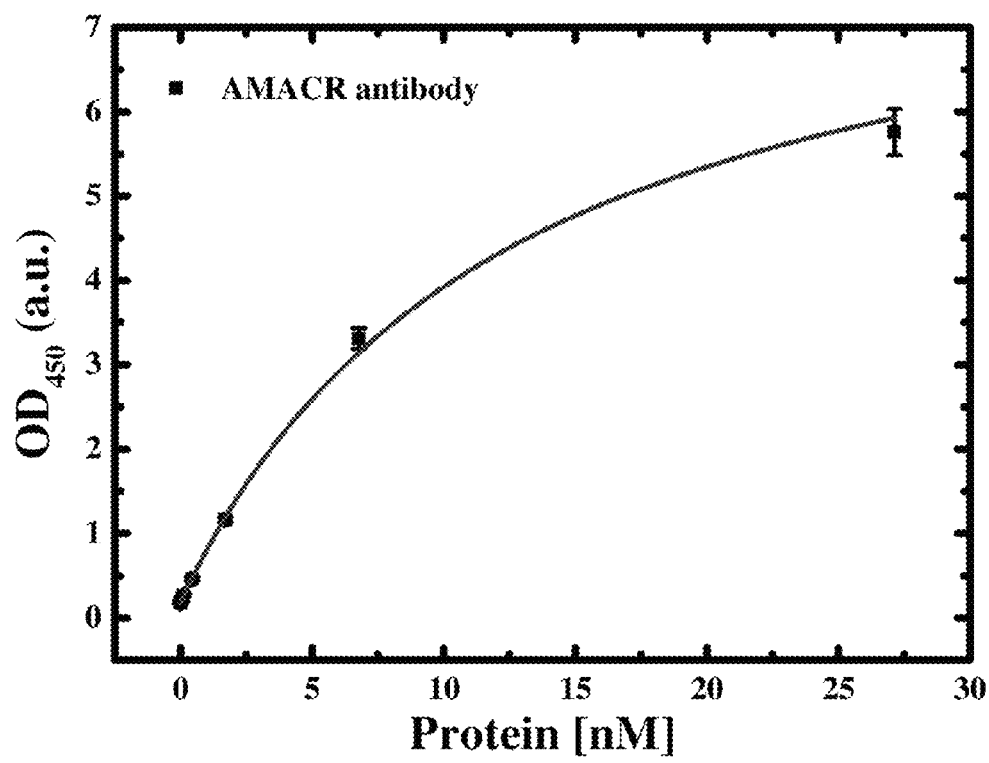
FIG. 2B shows ELISA tests of the homemade recombinant AMACR.

Homemade Recombinant AMACR Validation and Nanogram-Level AMACR Coating on a Single Epoxide-Functionalized Microbead for SELEX The SDS-PAGE analysis of the homemade recombinant AMCAR protein was shown in FIG. 2A, where a clear single band having a molecular weight of 45 kDa indicated that the recombinant product had the same molecular weight of AMACR. To further prove the successful expression of AMACR, an ELISA assay was performed using a mouse anti-human monoclonal AMACR antibody, a HRP-conjugated goat anti-mouse IgG polyclonal antibody, and TMB as the primary antibody, the secondary antibody, and the substrate, respectively, for the specific detection of AMACR. A dose-dependent ELISA response was shown in FIG. 2B and demonstrated that homemade AMACR protein could be detected by the anti-AMACR antibody like the commercial AMACR protein.

Figure 2C:
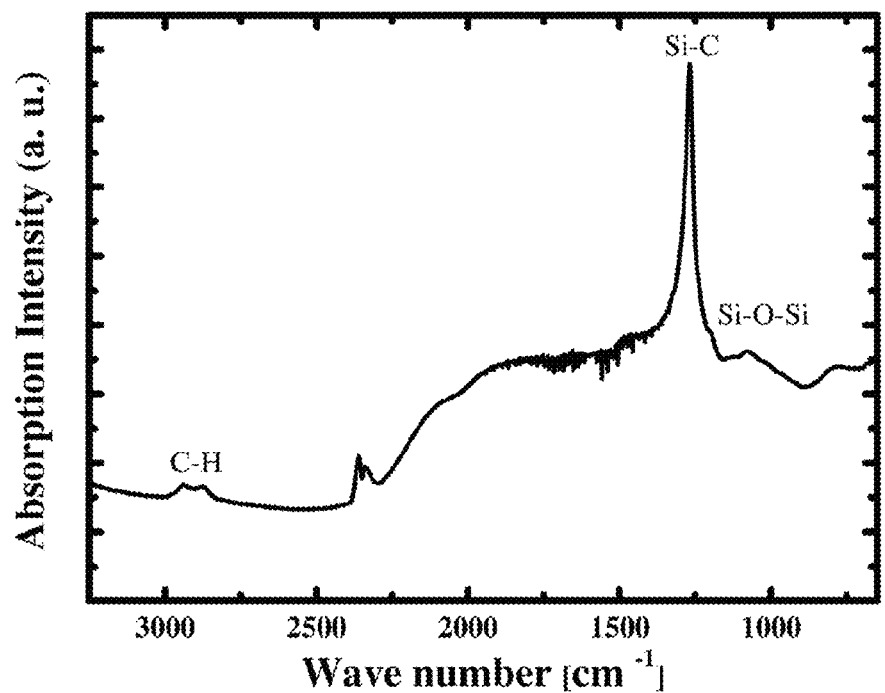
FIG. 2C shows a FTIR spectrum of EGBs, where unmodified glass microbeads are used to provide a reference spectrum.

In the present invention, single-bead SELEX method was performed and the method began with epoxide functionalization on 500 μm glass microbeads. The size of the bead allowed tweezers-based single-bead manipulation. A silane-based chemical reagent GLYMO was applied to modify the surfaces of the glass microbeads and yield the EGBs. FIG. 2C plotted the FTIR spectrum of the EGBs. The stretching vibration bands of the Si—O—Si, Si—$CH_3$, and C—H were present around 1110, 1270, and 2950 $cm^{-1}$, respectively. These bands proved that GLYMO had been successfully capped on the microbead surface.

Figure 2D:
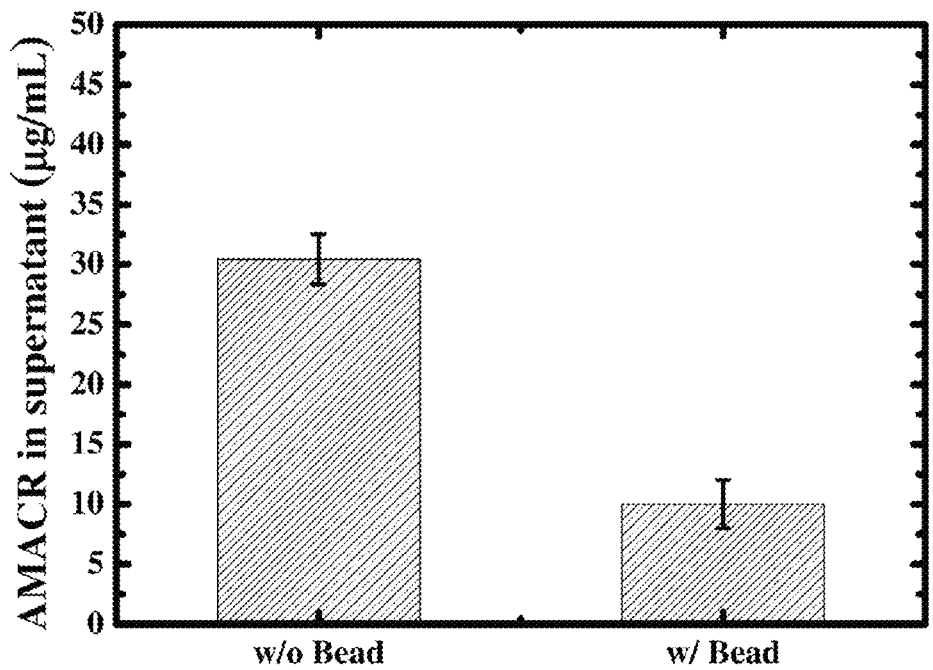
FIG. 2D shows the AMACR-binding capacity evaluation for EGBs ("w/o Bead": before the protein-binding reaction; "w/ Bead": after the reaction)

FIG. 2D compared the concentrations of the AMACR protein coating solution before and after the reaction with the epoxide-functionalized EGBs at 4° C. overnight by the Bradford assay. The amount of AMACR coated on the EGBs could be estimated accordingly by the difference between the two concentrations. The AMACR-binding capacity for each single EGB was calculated by dividing the amount of AMACR (ca. 600 ng) coated on the EGBs by the amount of loaded EGBs (30 mg=ca. 200 spheres) and was ca.3 ng AMACR per EGB. In the present embodiment, only three AMACR coated EGBs were used in a single SELEX round, so five SELEX rounds only consumed ca. 45 ng AMACR to accomplish the aptamer selection task. As a result, the SELEX protocol was beneficial and efficient for selecting aptamers against high-price and precious proteins.

Example 2

Materials and Methods

Reagents

Synthesized oligonucleotide sequences were purchased from Integrated DNA Technologies (Coralville, Iowa) and Purigo Biotech (Taipei, Taiwan). Real-time quantitative PCR kit was purchased from Qiagen (Venlo, Netherlands). PCR kit and Centri-Sep™ Spin Column were purchased from Life Technologies (Grand Island, N.Y.). Streptavidin magnetic bead was purchased from PerkinElmer (Waltham, Mass.). All the other reagents were of analytical grade. (Rochester, N.Y.). All other buffers and reagents are of the highest commercial purity.

Single-Bead SELEX

A SELEX round against AMACR-coated EGBs was illustrated in FIG. 1A. The 60-mer single-stranded DNA (ssDNA) library containing a centered 30 mer randomized sequence pattern (5'-CCCTACGGCGCTAAC-(N)$_{30}$-GC-CACCGTGCTA CAA-3') (SEQ ID NO: 2) was used. In the first SELEX round, three AMACR-coated EGBs were incubated with 2 nmol of the ssDNA library pre-dissolved in 20 μL of the selection buffer (diversity=1.2×10$^{15}$, heated to 95° C. for 5 min and gradually cooled to 25° C. before use) in a 200 μL PCR tube under a gentle agitation at 25° C. for 1 h. After the incubation step, the three beads were washed with 200 μL selection buffer six times and then were individually transferred by a pincette (i.e., a pair of tweezers) into a 25 μL PCR premix consisted of the Rotor-Gene SYBRs Green PCR kit (Qiagen), the forward primer (5'-CCCTACGGCGCTAAC-3') (SEQ ID NO: 3) and the biotin-labeled reversed primer (5'-(biotin)-TTGTAGCACG-GTGGC-3') (SEQ ID NO: 4). Then the DNA sequences bound onto the AMACR-coated beads were amplified and simultaneously quantified using a Qiagen q-PCR machine (Rotor-Genes Q) by a 5 min initial denaturation at 95° C. followed by 12 cycles of a rapid two-temperature PCR reaction (95° C. for 10 s and 60° C. for another 10 s). The biotinylated PCR amplicons were purified by incubation with streptavidin (SA)-coated magnetic beads in a 10×SSC buffer for 1 h with gentle shaking and then with twice washes in the same buffer. Not captured by the SA beads, the forward ssDNA strands were isolated in the presence of 50 mM NaOH. Exchanged buffer to the selection buffer by a Centri-Sep™ spin column, the ssDNA pool for the next SELEX round was obtained. The subsequent SELEX rounds were carried out iteratively according to the above procedure, except for adjusting the wash stringency to remove non-specific binding events right after the interaction between the ssDNA pool and AMACR-coated EGBs. The wash buffers were the selection buffers with 100 mM NaCl for the 1$^{st}$ and 2$^{nd}$ SELEX rounds, 300 mM NaCl for the 3$^{rd}$ and 4$^{th}$ rounds, and 500 mM NaCl for the 5$^{th}$ round. In addition, before incubation with the AMACR-coated beads, the ssDNA pool was counter-selected against thirty BSA-coated EGBs for SELEX round 2 to round 5. Also, a qPCR analysis on the non-specific binding event of an ssDNA pool to the BSA-coated beads was done for comparison with the specific-binding qPCR analysis. After five rounds of SELEX, the winning pool was harvested, cloned, and sequenced.

Results

Figure 3A:
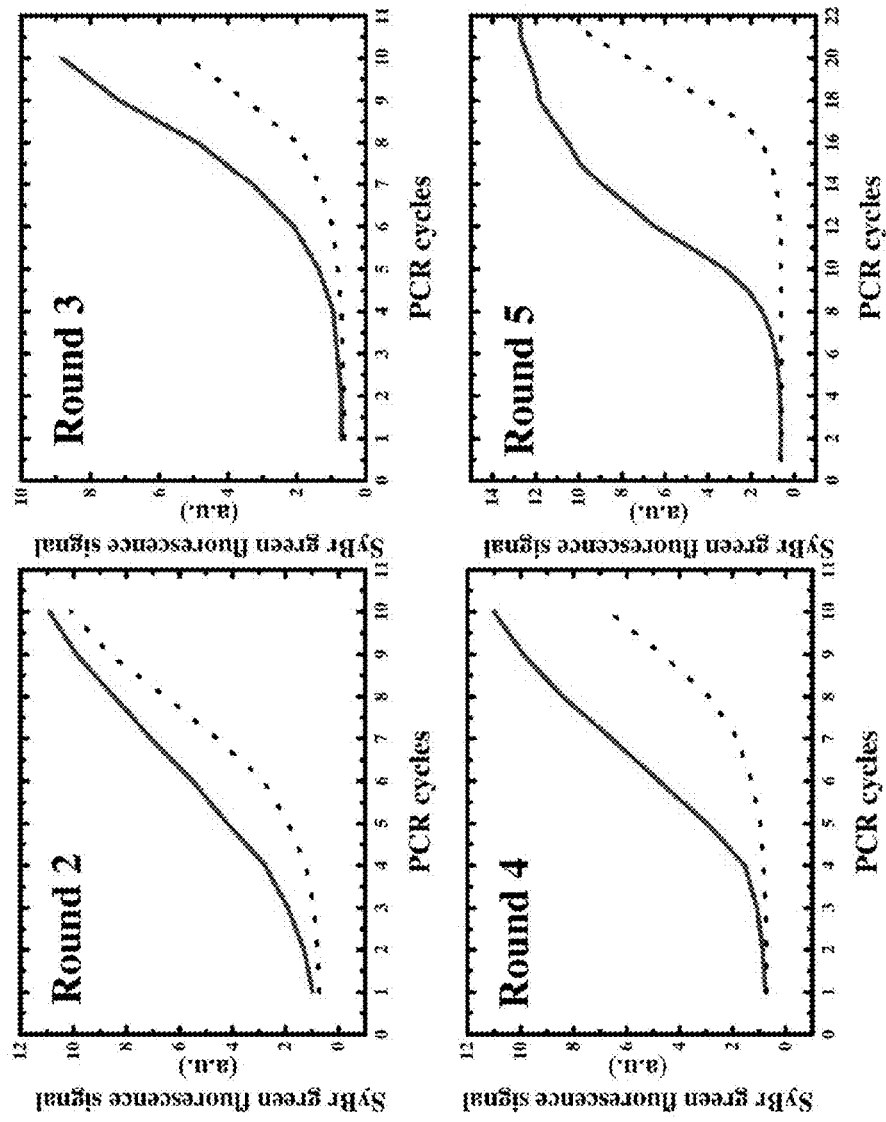
FIG. 3A shows a differential qPCR analysis for monitoring the ssDNA ligand evolution during the $2^{nd}$ to $5^{th}$ SELEX round. The specific ssDNA ligand binding to AMACR-coated beads (solid line) is compared with the non-specific ssDNA ligand binding to BSA-coated beads (dash black line) in each sub-figure.
Figure 3B:
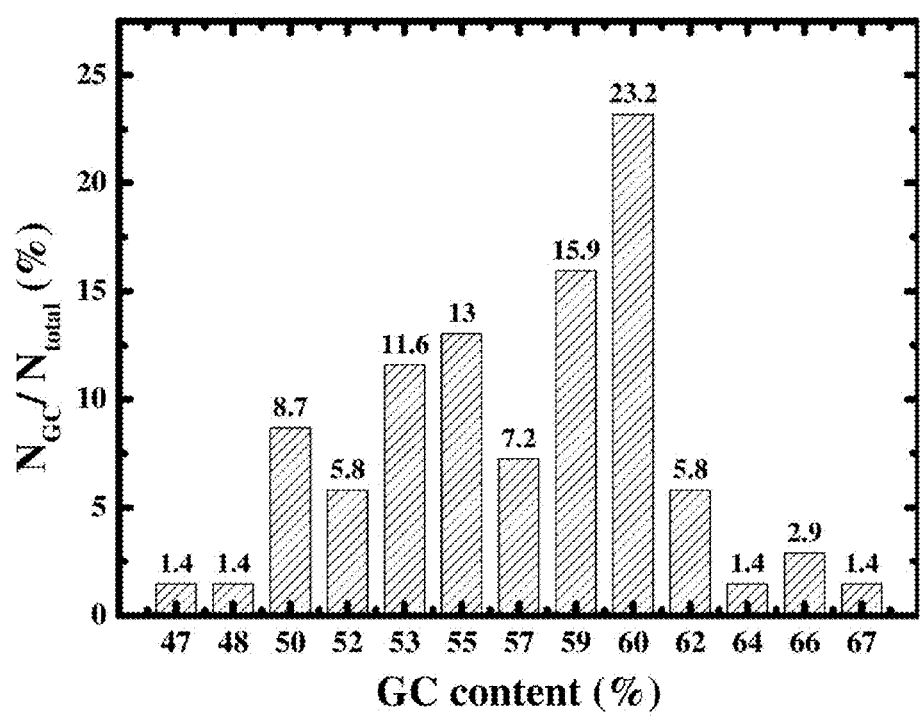
FIG. 3B shows the GC content distribution of 69 aptamer candidate sequences. $N_{GC}$ is the number of the aptamer with a specific GC content, and $N_{total}$ is the total number of aptamer candidates compared.

The Evolution of AMACR-Binding DNA Ligands Monitored by Differential qPCR Analysis During the SELEX rounds, the real-time qPCR technique was employed for both preparative (amplification of the ssDNA ligands) and analytical (quantification of the ssDNA ligands) purposes. The reporter used for qPCR was SYBR Green I. FIG. 3A presented the results of comparative qPCR quantification data for the specific ssDNA ligands bound to the AMACR-coated beads with respect to the non-specific ssDNA molecules bound to the BSA-coated beads for SELEX rounds 2-5. The obvious increase of ΔCt (the threshold PCR cycle difference) between two groups with the SELEX round number implied that the specific ssDNA ligands had been evolved and enriched in the SELEX process. FIG. 3A also showed that the qPCR fluorescent signal could be detected in early PCR cycles (i.e. low Ct values). This meant that the real-time qPCR method was sensitive enough for monitoring the ssDNA ligand evolution in the single-bead SELEX process. (Note: it should be noted that only a single bead was interrogated with the qPCR analysis.) The qPCR data for the specific binding event in the fifth SELEX round showed an obvious delay in Ct as compared to those of earlier rounds. This resulted from highly stringent washes (with 500 mM NaCl). Meanwhile, it could be observed that the differential qPCR analysis in the fifth round gave the largest different in Ct values, which showed that the ratio of specific-binding ligands (bound to AMACR) to non-specific molecules (bound to BSA) was greater than 1000. To avoid the "over-selection" problem that caused the PCR bias and artifacts, the ssDNA pool from the 5$^{th}$ round was considered as the winning pool for cloning, sequencing and analysis. In the present embodiment, 69 clones of the ssDNA ligands were sequenced. The GC content distribution was plotted as a histogram in FIG. 3B. The results showed that there were 88.5% of the DNA sequences with a GC content greater than 50%, and almost half of the sequences had a GC content ranging between 57% and 62%.

Example 3

Materials and Methods

Sequence Alignment, Secondary Structure Prediction and Circular Dichroism Characterization Sixty-nine clones from the winning ssDNA pool were prepared and sequenced according to the common SELEX practice. A general DNA multiple sequence alignment online program, ClustalW2, was used to align the 69 DNA sequences. From the multiple sequence alignment analysis, three groups with higher alignment score were identified, and one of each group was picked up as the representative aptamer candidates. The second structures of the aptamer candidates were then predicted by the online program RNAstructure Version5.6 with the DNA mode.

Five micro molar aptamer samples were prepared in the selection buffer. The CD spectra were recorded at 25° C. in a 0.1 cm path length cuvette. The parameters were set as follows: sensitivity was 100 mdeg, data pitch was 1 nm, response was 1 s, band width was 1 nm, and scanning mode was continuous scanning with a scanning speed of 50 nm/min. The reported CD spectra were averaged over three scans, from wave lengths of 320 to 200 nm.

Results

The Aptamer Sequences and Their Structural Characteristics

The 69 candidate sequences were analyzed by a typical multiple sequence alignment tool (ClustalW2). The sequence alignment score telling the similarity or consensus between the SELEX products was used as the criterion for choosing three representative aptamer sequences out of the 69 sequences for AMACR assays. The aptamer sequences with top five scores were listed as Table 1, where the N30 domains were bold type.

TABLE 1 the aptamer candidate sequences with highest alignment scores.

| Name | SEQ ID NO: | Sequence (5' to 3') | ΔG$_{37°\ C.}$ (kcal/mol) |
|---|---|---|---|
| AMC51 | 5 | 5'-CCCTA CGGCG CTAAC CCATG CTACG AATTC GTTGT TAAAC AATAG GCCAC CGTGC TACAA-3' | −5.7 |

TABLE 1-continued the aptamer candidate sequences
with highest alignment scores.

| Name | SEQ ID NO: | Sequence (5' to 3') | $\Delta G_{37°\,C.}$ (kcal/mol) |
|---|---|---|---|
| AMC55 | 6 | 5'-CCCTA CGGCG CTAAC CAGTA TGTTC CGGAT TGGAG AGCTC CTGTT GCCAC CGTGC TACAA-3' | -5.3 |
| AMC56 | 7 | 5'-CCCTA CGGCG CTAAC CCAGC TACTC TAGAA CCCAT TATAT TTTGG GCCAC CGTGC TACAA-3' | -8.9 |
| AMC68 | 8 | 5'-CCCTA CGGCG CTAAC CATGA CGAAT TGTGT ATATA TCAAT ACTCG GCCAC CGTGC TACAA-3' | -4.3 |
| AMC69 | 9 | 5'-CCCTA CGGCG CTAAC ACTAC TCTTC CGGAT GAAGC TCTTA TGTTG GCCAC CGTGC TACAA-3' | -7.2 |

The N30 domains are bold type

Figure 4A:
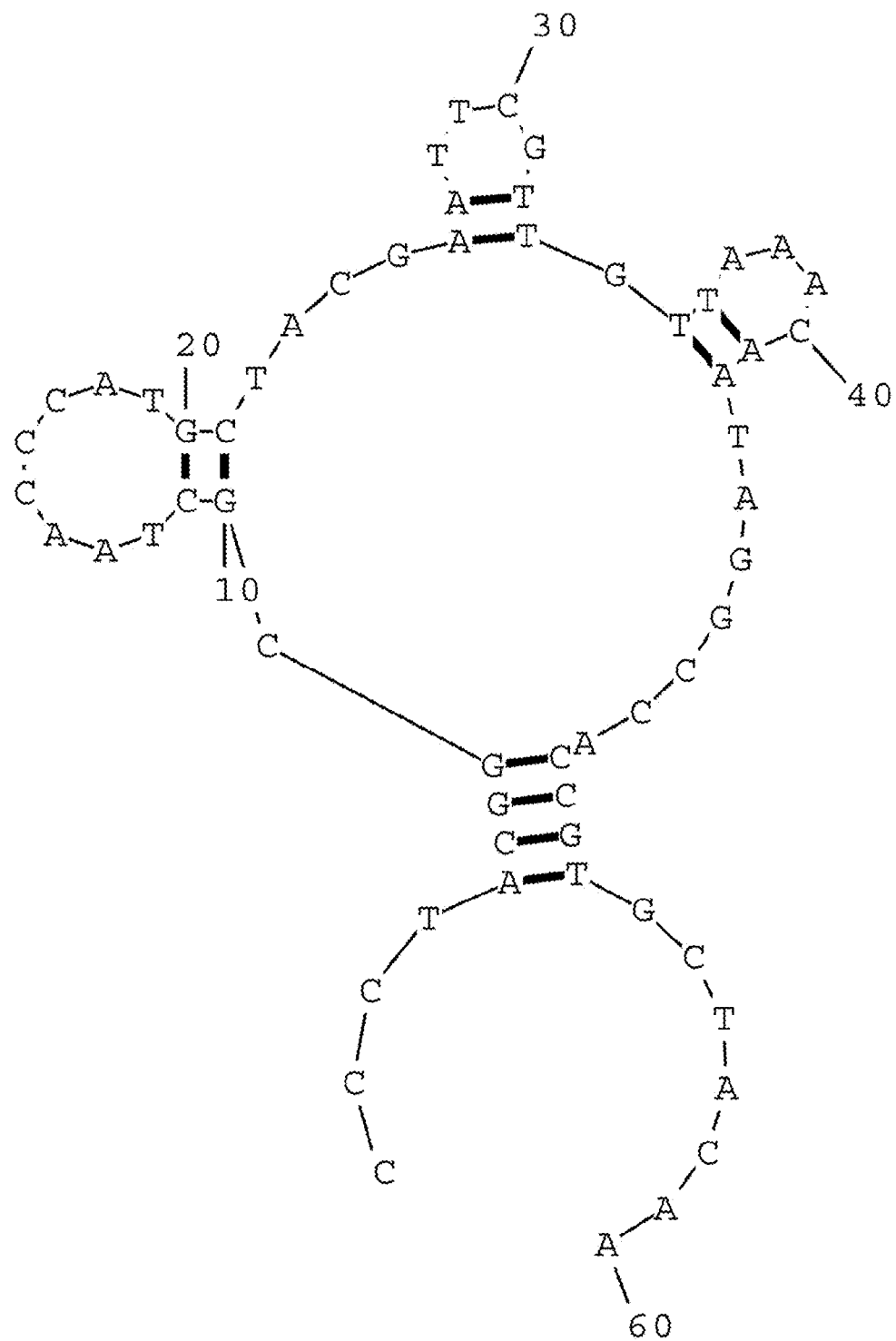
FIG. 4A shows a $2^{nd}$ structure prediction for the aptamer AMC51 (SEQ ID NO: 5).
Figure 4B:
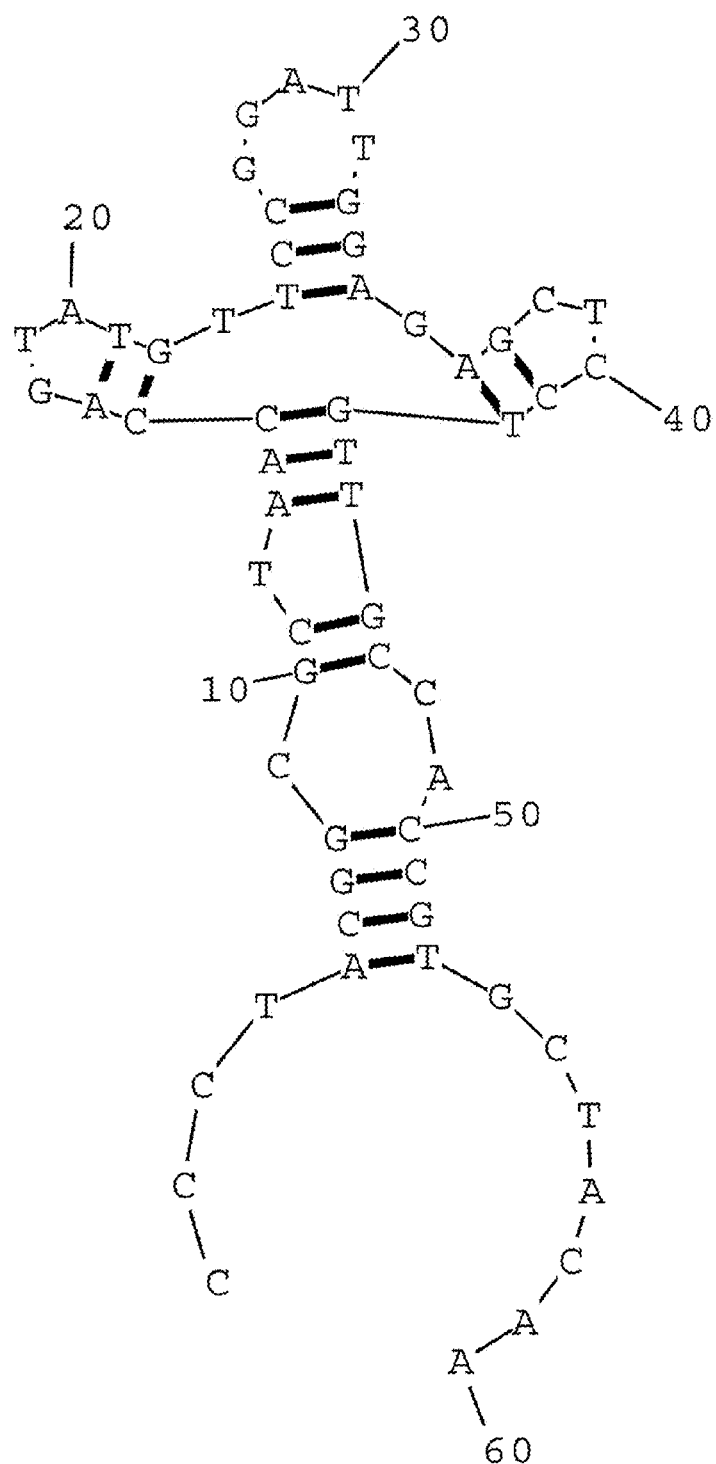
FIG. 4B shows a $2^{nd}$ structure prediction for the aptamer AMC55 (SEQ ID NO: 6).
Figure 4C:
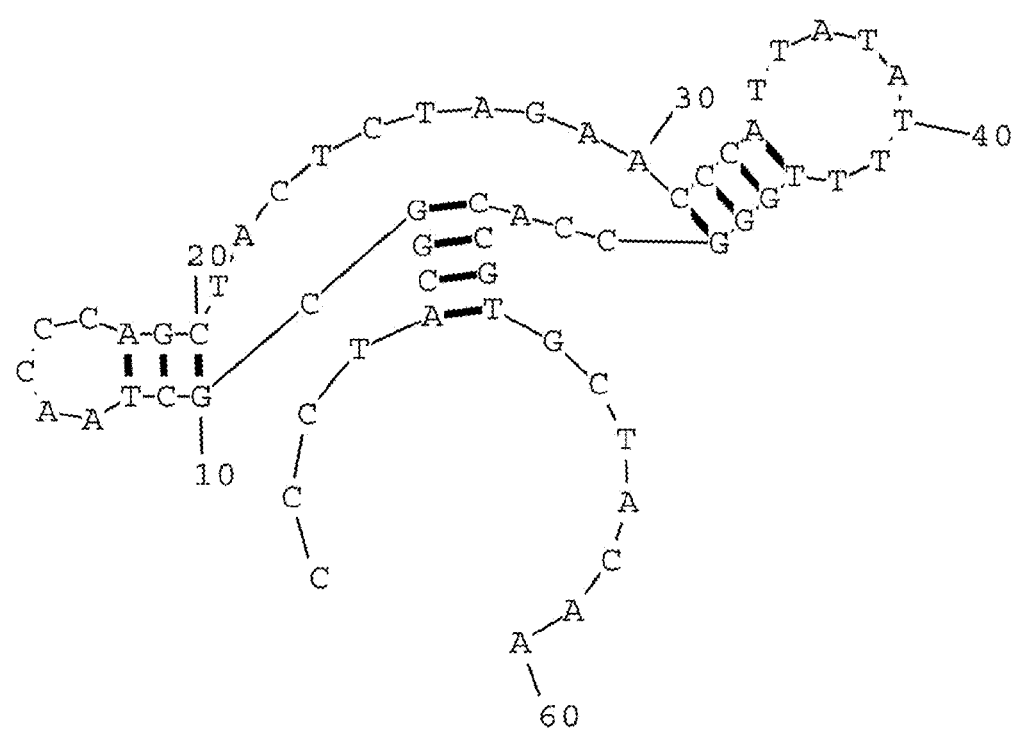
FIG. 4C shows a $2^{nd}$ structure prediction for the aptamer AMC56 (SEQ ID NO: 7).
Figure 4D:
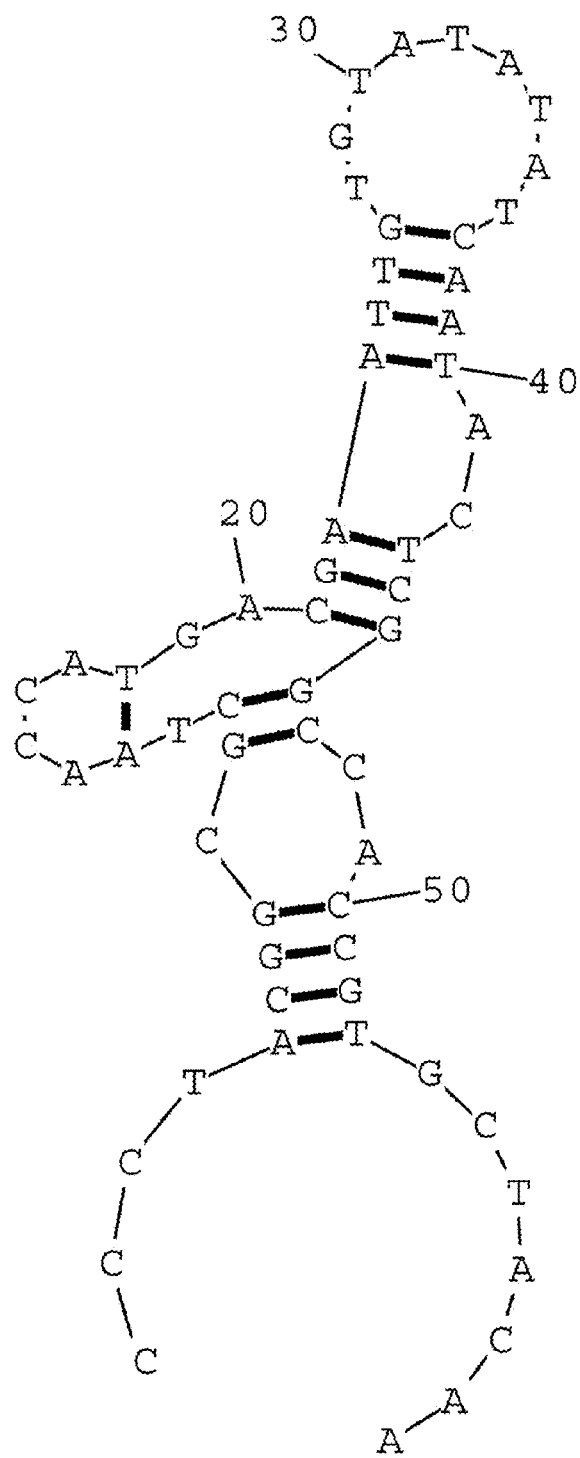
FIG. 4D shows a $2^{nd}$ structure prediction for the aptamer AMC68 (SEQ ID NO: 8).
Figure 4E:
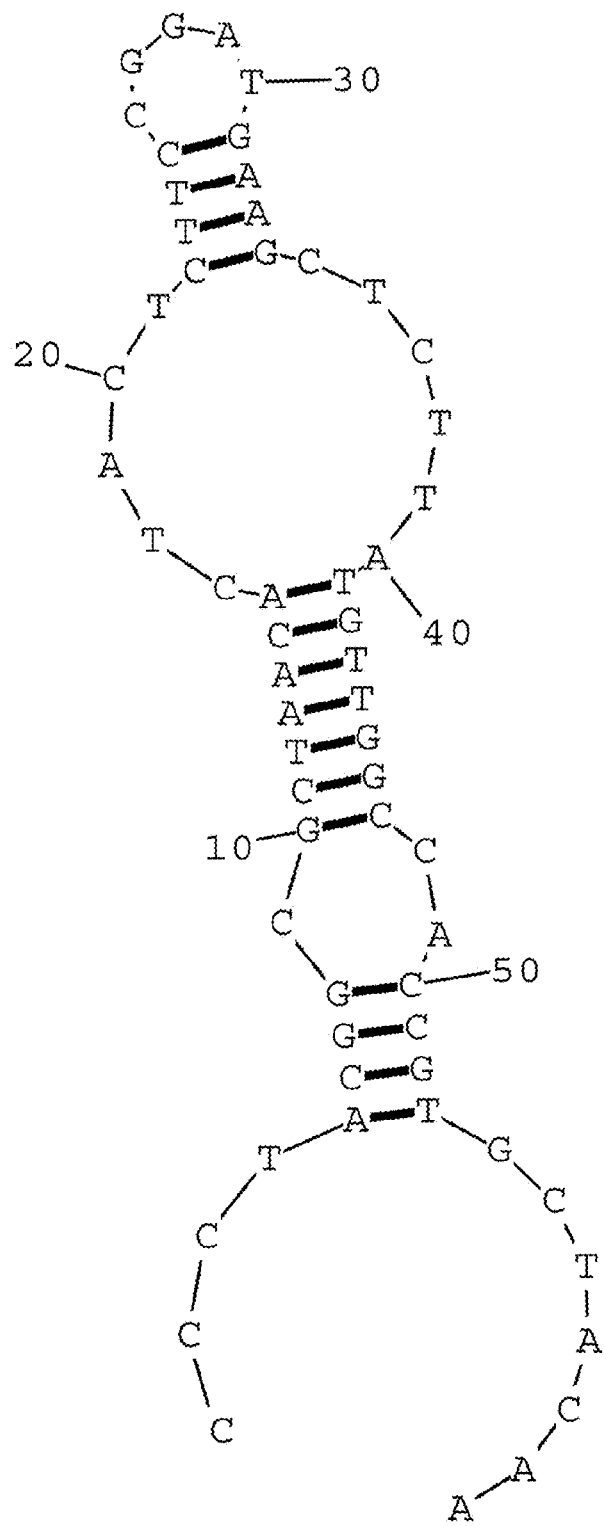
FIG. 4E shows a $2^{nd}$ structure prediction for the aptamer AMC69 (SEQ ID NO: 9).
Figure 4F:
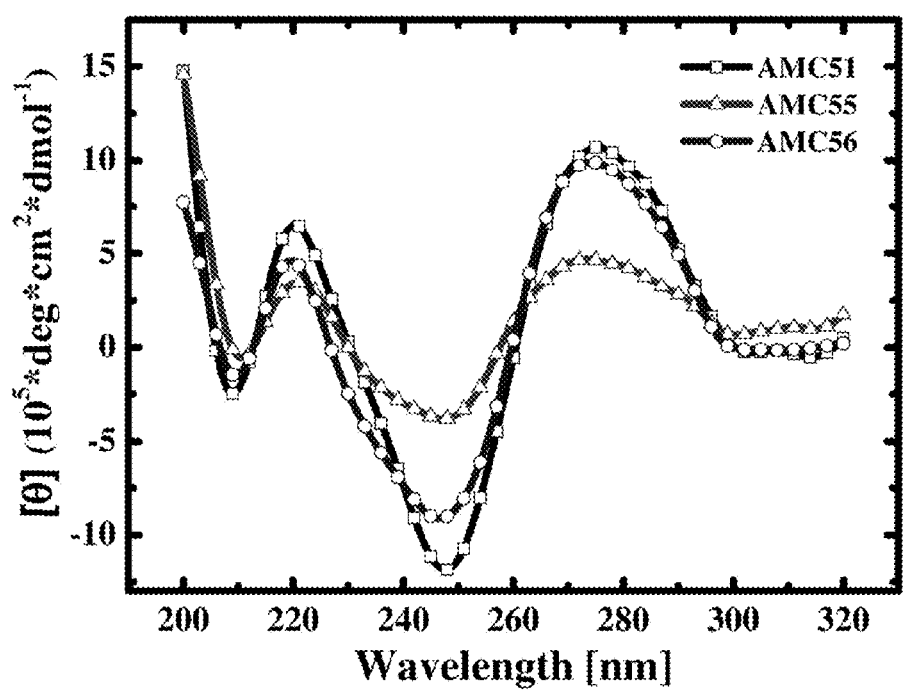
FIG. 4F shows a CD spectra for the aptamers (AMC51, AMC55, and AMC56).

The secondary structures of the five aptamers were predicted by RNA structure version 5.6 (DNA mode) and were plotted in (FIGS. 4A, 4B, 4C, 4D, and 4E), which featured multiple stem-loop structures as well as intra-molecular variants of the B-form structure. The delta Gibbs free energy (AG) estimates were between −4.3 and 8.9 kcal/mol at 37° C. indicating that these aptamer structures were stable. FIG. 4F compared the CD spectra of the three aptamers (AMC51, AMC55, and AMC56) in the selection buffer. As could be seen, the CD spectra of the aptamers all had two positive bands around 220 and 275 nm and a negative band around 210 and 245 nm. This data proved that the aptamer structures belong to a subtype of B-form secondary conformation, which was consistent with the in silico structural prediction given in FIGS. 4A, 4B, 4C, 4D, and 4E. However, different from the predicted AG values listed in Table 1, FIG. 4F showed that AMC55 (SEQ ID NO: 6) was least able to form as table B-form or stem-loop binding motif while compared to the other two. In addition, AMC51 (SEQ ID NO: 5) had more obvious (more stable) B-form characteristics than AMC56 (SEQ ID NO: 7).

Example 4

Materials and Methods

Reagents

Bovine serum albumin (BSA), human serum albumin (HSA), and RIPA buffer, were all purchased from Sigma-Aldrich (St. Louis, Mo.). Commercial AMACR protein human recombinant was purchased from ProSpec-Tany TechnoGene (Rehovot, Israel). Fetal bovine serum (FBS) was purchased from Life Technologies (Grand Island, N.Y.). Alkaline phosphatase-conjugated streptavidin (Strep-AP) was purchased from Abcam (Cambridge, Mass.). AttoPhos® AP fluorescent substrate system components was purchased from Promega (Madison, Wis.). Clear and black opaque 96 well polystyrene plates were purchased from Nunc™ A/S (Rochester, N.Y.). All the other reagents were of analytical grade. (Rochester, N.Y.). All the other reagents were analytical grade. All other buffers and reagents were of the highest commercial purity.

Enzyme-Linkedaptamerassays (ELAAs)

Enzyme-linked aptamer assays with typical black opaque 96-well polystyrene microtiter plates that resembled ELISA assays were carried out for (1) assessment of the affinity and specificity of the selected AMACR binding aptamers and (2) proof-of-concept fluorescent AMACR detection using aptamers. For the first task, varied concentrations of aptamers were tested with a constant protein concentration (0.2 μM); for the second task, varied concentrations of proteins were detected using a constant aptamer concentration (500 nM). Both used the following ELAA protocol unless otherwise noted. For protein coating, AMACR diluted in 0.05 M sodium carbonate buffer (pH9.6) was added to the wells of the plates (100 μL/well) and incubated at 4° C. overnight. After incubation, the wells were washed three times with 200 μL/well of selection buffer containing 0.05% Tween 20. For blocking, each AMACR-coated well was added with 200 μL of 3 wt % BSA in the selection buffer containing 0.05% Tween 20 and was then incubated at 37° C. for 2 h. Afterward, wells were washed as previously described. Before protein assays, biotin-labeled aptamer sequences were suspended in the selection buffer, heated to 95° C. for 5 min, and gradually cooled to 25° C. Then each protein-coated well was added with 100 μL of aptamer solution (in the selection buffer) and was incubated at room temperature for 1 h followed by the same wash procedure. After that, each well was added with two drops (ca. 100 μL) of an alkaline phosphatase-conjugated streptavidin (Strep-AP) solution (0.003 mg/mL) (Abcam) and incubated at room temperature for 30 min followed by the washes. For fluorescent signal development, each well was added with 100 μL of AttoPhos® AP fluorescent substrate solution (Promega) and incubated in dark for at least 15 min. Finally, the fluorescent signal of each well was read by a fluorescent microplate reader (excitation at 435 nm and emission at 555 nm).

Results

Figure 1B:
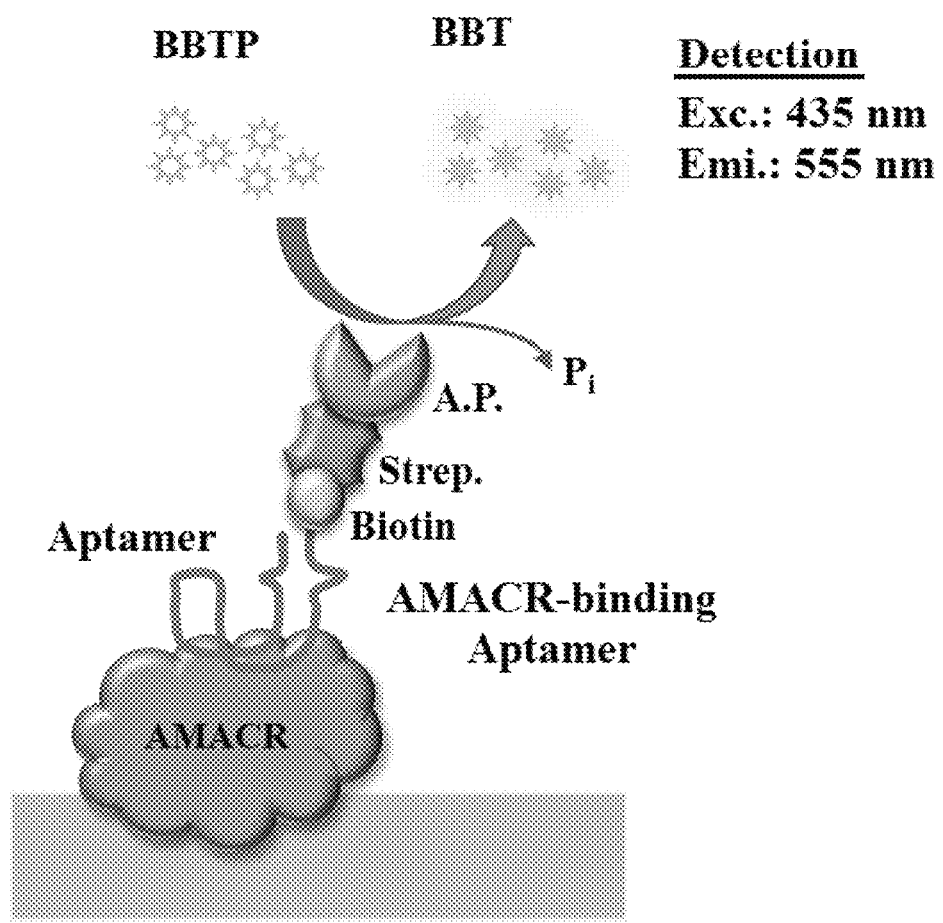
FIG. 1B shows a schematic illustration of the fluorescent ELAA detection of AMACR, where BBTP is 2'-(2-benzothiazolyl)-6'-hydroxybenzothiazole phosphate; BBT is 2'-(2-benzothiazolyl)-6'-hydroxybenzothiazole; A.P. is alkaline phosphatase.

Nanomolar-Level Affinity and High-Specificity for AMACR Recognition and Toward Subnanomolar-Level AMACR Detection by a Fluorescent ELAA Method A series of florescent ELAA experiments were performed to assess the AMACR binding affinity and specificity of the aptamers AMC51, AMC55, and AMC56. The principle of the ELAA detection, which was similar to a standard ELISA method except for replacing a primary antibody by an aptamer, was schematically illustrated in FIG. 1B. The AttoPhos® AP fluorescent substrate (2'-[2-benzothiazoyl]-6' hydroxybenzothiazole phosphate, BBTP) was used as the reporter to enhance the detection sensitivity.

Figure 5A:
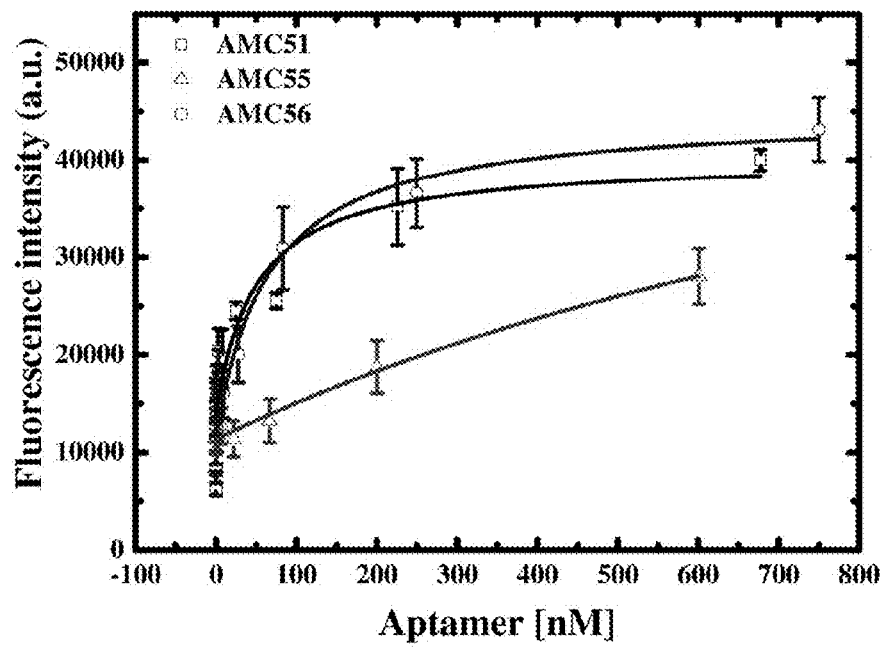
FIG. 5A shows ELAA-based total-binding assays for the binding affinity estimation of the AMACR recognition aptamers (AMC51, AMC55, and AMC56).
Figure 5B:
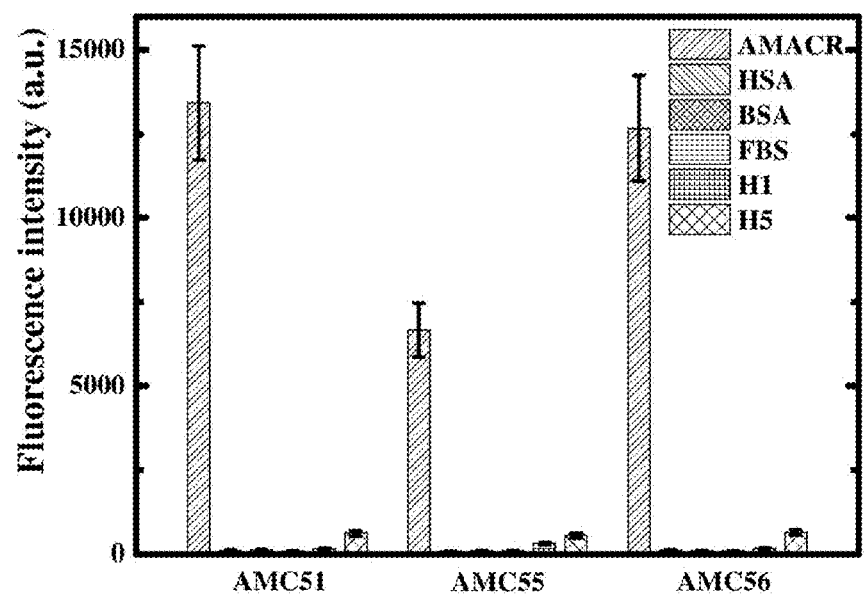
FIG. 5B shows ELAA-based assessment for the binding specificity of the AMACR recognition aptamers. The concentration of aptamers tested are all 0.5 μM, and the concentration of the proteins tested are all 0.2 μM.
Figure 6:
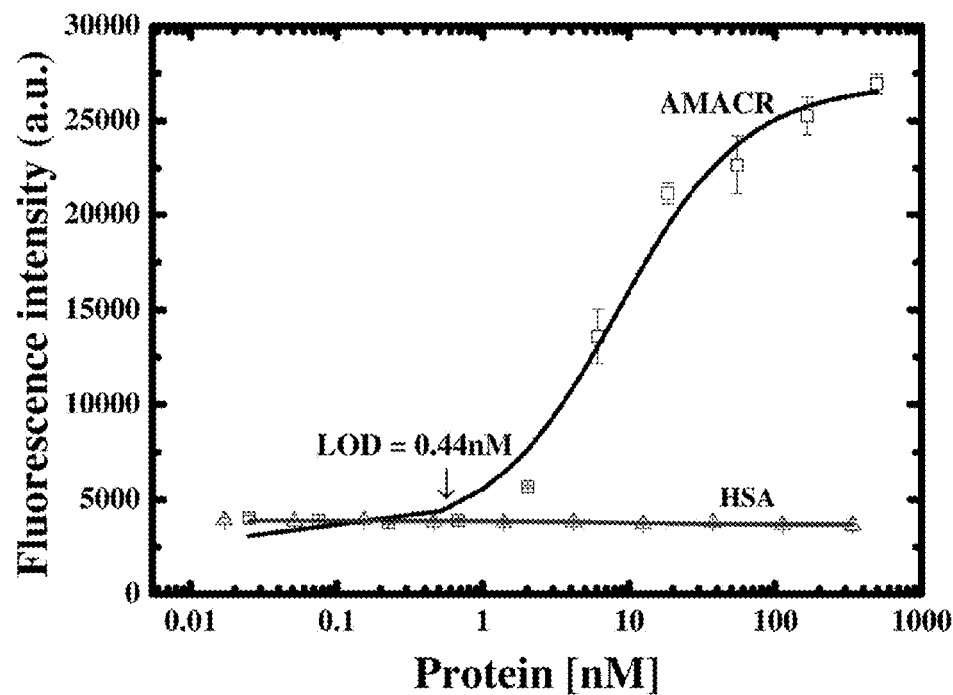
FIG. 6 shows a result of the fluorescent ELAA-based AMACR detection using the aptamer AMC51. The aptamer concentration is 0.5 μM.
Figure 7:
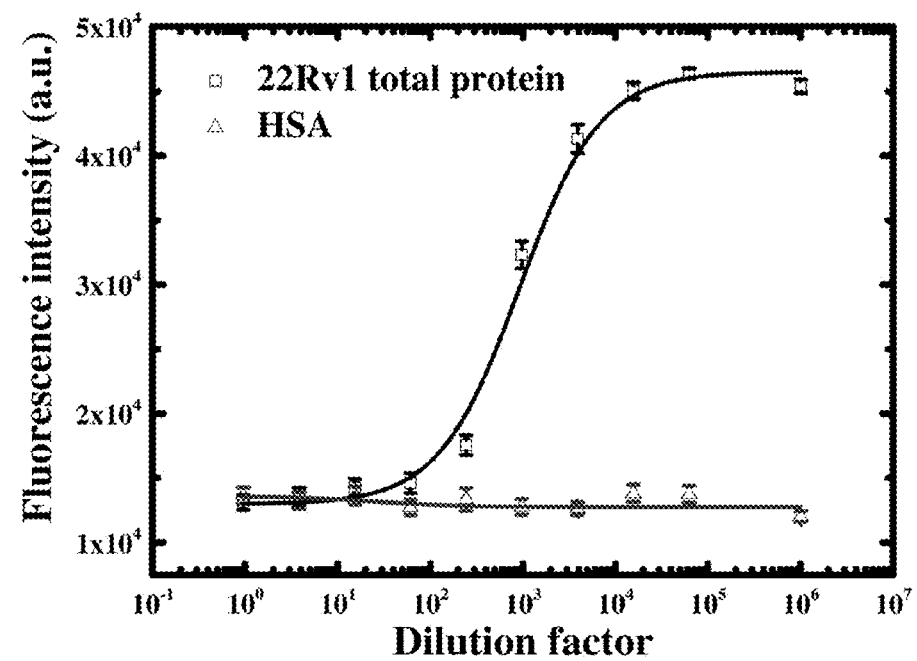
FIG. 7 shows a result of the fluorescent ELAA-based detection of a dilution series of the cellular lysate of a prostate cancer cell line 22Rv1, which is known to over-express AMACR. The aptamer concentration is 0.5 µM.

FIG. 5A represented the results of the equilibrium AMACR total binding assays using the fluorescent ELAA format for AMC51, AMC55, and AMC56. From this data, the apparent dissociation constants (KD) for the binding events between AMACR and AMC 51, AMC55, and AMC56 with AMACR were estimated to be 49±26 nM, 139±157 nM, 65±31 nM, respectively. It could be seen that the single-bead SELEX protocol was not only efficient but also able to generate high-affinity aptamers. In addition, the trend of the KD value was consistent with the trend of the obviousness of the CD features shown in FIG. 4F. This implied that the AMACR protein preferred binding to an aptamer with a stable, preformed secondary structure rather than binding to an aptamer structure with less stability. We also used the same ELAA approach for analysis of the cross-reactivity of the aptamers with other proteins. Since a non-specific binding event would be more frequently encountered at a higher aptamer concentration, we used 500 nM aptamer rather than a lower-concentration aptamer for the cross-reactivity test. The results were plotted in FIG. 5B. It could be found that all of the three aptamers tested were highly specific to AMACR and did not bind to non-target proteins, such as bovine serum albumin (BSA), human serum albumin (HSA), total protein infetal bovine serum (FBS), and other recombinant E. coli proteins like hemagglutinin 1 (H1), hemagglutinin 5 (H5). Again, AMC51 performed the best, while AMC56 tightly followed and AMC55 was left behind. This evidenced that aptamers in the present invention were highly specific to AMACR. Using the best aptamer (AMC51), the present invention demonstrated the first fluorescent ELAA detection of AMACR, the emerging prostate cancer biomarker. The experimental result was given in FIG. 6 based on the same detection principle of FIG. 5 illustrated in FIG. 1B. Different from FIG. 5A, in which the ELAA assayed varied aptamer concentrations with a constant AMACR concentration (0.2 µM), FIG. 6 reported an assay detecting different protein concentration with a fixed aptamer concentration (500 nM). It could be seen in FIG. 6 that aptamer-based fluorescent AMACR assay featured a wide dynamic range (from $10^{-1}$ to $10^3$ nM, corresponding to a highly differentiable AMACR dose-responsive property ranging from ca. 0.5 nM to 500 nM) and high AMACR specificity (no significant cross-reactivity with HSA). To estimate the limit of detection (LOD) of the ELAA detection, the limit of blank (LOB) was estimated according to the following equation: LOB=$Mean_{blank}$+1.645 ($SD_{blank}$), where $Mean_{blank}$ was the average signal and $SD_{blank}$ was the standard deviation of the blank sample signal (containing no AMACR). Then, the LOD was estimated by LOD=LOB+1.645 ($SD_{low\ concentration\ sample}$), where SD low concentration sample was the standard deviation of the diluted sample signal (containing low-concentration AMACR). According to this method, the LOD was determined to be as low as 0.44 nM (19.5 ng/mL). It was reported that the concentration of AMACR in blood from patients with prostate cancer was in sub-µM (µg/mL) range (World J Urol. 2010 December; 28 (6): 681-6). The aptamer (AMC51) was not only responsive to the recombinant AMACR but also responsive to the cellular lysate (total protein) of a common prostate cancer cell line 22Rv1 that over-expresses AMACR (FIG. 7). This meant that ELAA method met the requirement of AMACR detection for the application in prostate cancer diagnosis.

Example 5

Methods

AMACR Detection in Cell Lysates

Total proteins from two common prostate cancer cell lysates (LNCaP and PC3) were used as target samples for the ELAA assay with AMC51 aptamer. In sample preparations, each total protein was diluted to 100 ng/µL in the selection buffer (pH 8), then loaded to the microtiter plate (50 µL/well), and incubated at 4° C. overnight before the ELAA assay.

After incubation, the wells were washed three times with 200 µL/well of selection buffer containing 0.05% Tween 20 (TBST). For blocking, each AMACR-coated well was loaded with 200 µL of 3 wt. % BSA in the TBST, and incubated at 37° C. for 2 hours. Afterward, wells were washed as previously described. Before protein assays, biotin-labeled AMC 51 aptamer was diluted to 0.2 µM in the selection buffer (pH 7.4), then heated to 95° C. for 5 min, and gradually cooled to 25° C. Each protein-coated well was added with 100 µL of aptamer solution and incubated at room temperature for 1 hours followed by the same wash procedure.

After that, each well was loaded with two drops (ca. 100 µL) of an alkaline phosphatase-conjugated streptavidin (Strep-AP) solution (0.003 mg/mL) (Abcam) and incubated at room temperature for 30 min followed by the washes. For fluorescent signal development, each well was loaded with 100 µL of AttoPhos® AP fluorescent substrate solution (Promega) and incubated in dark for at least 15 min. Finally, the fluorescent signal of each well was read by a fluorescent microplate reader, FlexStation 3 (excitation at 435 nm and emission at 555 nm).

Results

AMACR Detection in Cell Lysate

The LNCaP and PC3 are both the prostate cancer cells, and it has been reported that the AMACR expression of LNCaP was higher than PC3. To identify AMC51 had enough specificity to distinguish different prostate cancer cells with distinct expression amounts of AMACR, AMC51 was used as a probe to detect the AMACR in LNCaP and PC3 cell lysates. The response from LNCaP cell lysate was normalized to 100, and the response from PC3 cell lysate was proportionally adjusted. The normalized data was shown in FIG. 8. From the results, it could be found the response from LNCaP cell lysate was higher than PC3. It represented the AMC51 could successfully identify the expression amounts of AMACR in different prostate cancer cell lines.

Example 6

Methods

Immunofluorescence of Human Prostate Cancer Cell Lines

For cell fixation, 22Rv1 cell, which cultured on a glass slide, was washed with 1× phosphate-buffered saline (PBS), pH 7.4, then treated by 3.7% formaldehyde solution in PBS for 10 minutes at room temperature, and finally washed two or more times with PBS. Before staining, the slide was placed in acetone at −20° C. for 3 to 5 minutes. For actin staining, diluted 5 µL rhodamine phalloidin (stock concentration: 200 units/mL); Life Technologies) into 200 µL 1×PBS with 1% bovine serum albumin (BSA), then the staining solution was loaded on the cell-fixed slide for 20 minutes at room temperature, and the slide was washed two or more times with PBS. For nuclear staining, DAPI was diluted to 300 nM in 1×PBS, then loaded on the slide for 10 minutes at room temperature, and the slide was washed two or more times with 1×PBS. Before AMACR staining, FAM-labeled AMC 51 aptamer was diluted to 1 µM in the selection buffer (pH 7.4), and heated to 95° C. for 5 min, and gradually cooled to 25° C. Afterwards, the aptamer solution was loaded on the slide for 1 hour at room temperature, and the slide was washed two or more times with selection buffer. The confocal images were taken using Leica TCS SP5 II confocal microscope.

Results

Immunostaining of Human Prostate Cancer Cell Lines

Figure 9:
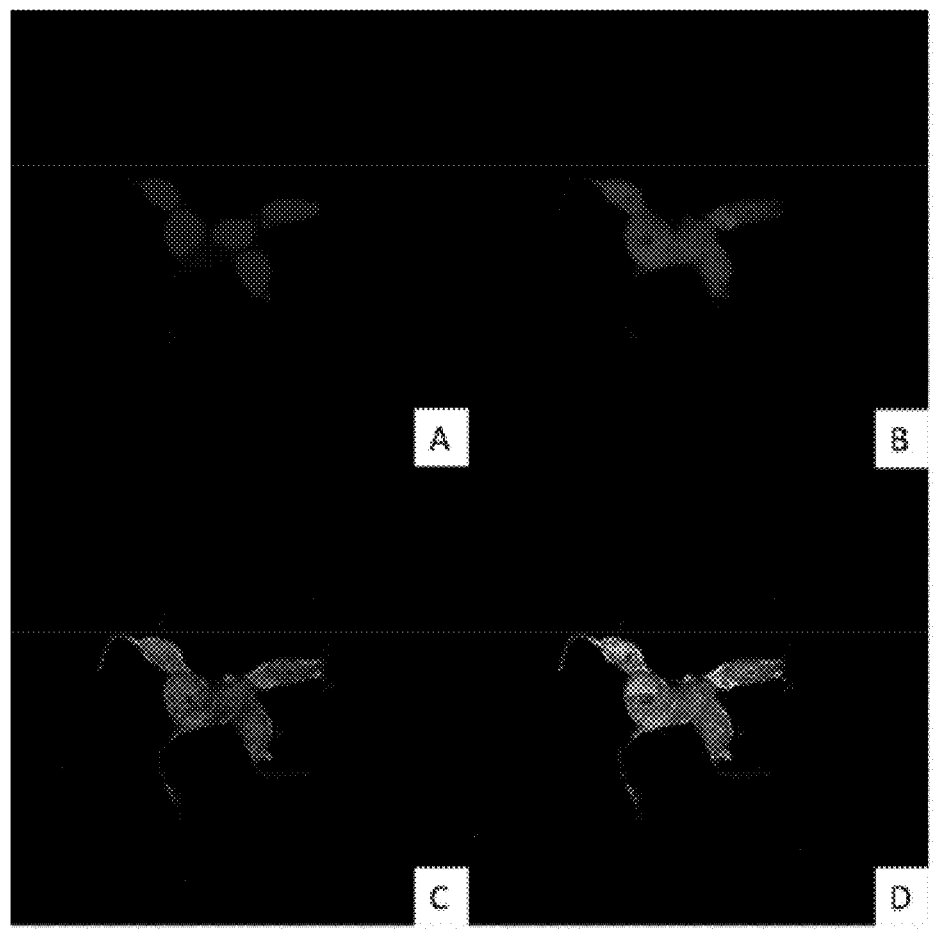
FIG. 9 shows an immunofluorescence analysis of 22Rv1. The images of (A) to (C) show the cells treated with DAPI (A), Rhodamine phalloidin (B), and FAM-AMC51 (C). The image of (D) shows a merged of the image of (A), (B), and (C).

Until today, the AMACR immunostaining mainly uses the antibody as the probe to detect the AMACR in prostate cancer cells or tissues. The present invention used the AMACR aptamer, AMC51, to replace the role of the antibody in AMACR immunostaining. FIG. 9 showed the immunofluorescence analysis of the 22Rv1 cell, a prostate cancer cell line. DAPI and rhodamine phalloidin could stain the nuclear and actin in cells, respectively. The confocal images of DAPI and rhodamine phalloidin were shown in FIG. 9 (A) and FIG. 9 (B), respectively. From these two images, the locations of the nuclear and cytoplasmic domain in the 22Rv1 cell could be identified. In previous literature for AMACR study, it had been reported that AMACR was localized in mitochondria and peroxisomes, which were organelles in cytoplasmic matrix. FIG. 9 (C) showed the confocal image of the 22Rv1 cell stained with the AMACR aptamer, AMC51. From the image, it could be observed the AMC51 could successfully stain the cytoplasmic domain in the 22Rv1 cell. FIG. 9 (D) showed the overlay of above confocal images, it showed obvious fluorescence signal aggregation of FAM label-AMC51 (green) in some parts of cytoplasmic domain, and these signal dots could form the stained-AMACR in the mitochondria and peroxisomes.

Figure 8:
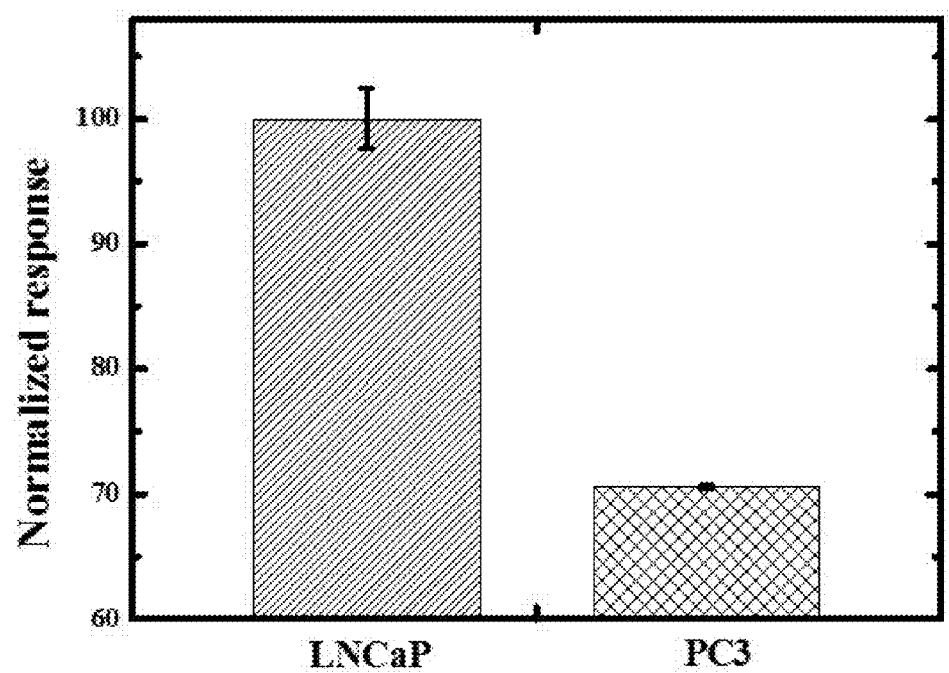
FIG. 8 shows an ELAA analysis for AMACR protein expression in the prostate cancer cell lysates; LNCaP (slash) and PC3 (mesh).

From the results of FIG. 8 and FIG. 9, it could be known that the aptamers of the present invention could identify the expression amounts of AMACR among different prostate cancer cell lines, and had a potential to replace the role of AMACR antibody in the applications of immunohistochemistry for prostate cancer diagnostics.

What is claimed is:

1. An alpha-methylacyl-CoA racemase binding aptamer which is selected from SEQ ID NO: 5, SEQ ID NO: 6, SEQ ID NO: 7, SEQ ID NO: 8, or SEQ ID NO: 9.

2. A kit for detecting alpha-methylacyl-CoA racemase or cancer in a sample comprising an alpha-methylacyl-CoA racemase binding aptamer, wherein the aptamer is selected from SEQ ID NO: 5, SEQ ID NO: 6, SEQ ID NO: 7, SEQ ID NO: 8, or SEQ ID NO: 9.

3. The kit of claim 2, which further comprises a detectable label on the aptamer, wherein the detectable label is selected from the group consisting of a radioisotope, an enzyme, a fluorescent tag, a chemiluminescent tag, and a magnetic substance.

* * * * *